United States Patent [19]

Matsui et al.

[11] Patent Number: 5,612,135
[45] Date of Patent: Mar. 18, 1997

[54] PAINT-FILM PROTECTIVE SHEET

[75] Inventors: Komaharu Matsui; Takeshi Eda; Mitsuo Wakimoto, all of Kanagawa; Kenichi Shibata, Osaka; Toshitaka Suzuki, Osaka; Mitsuyoshi Shirai, Osaka; Kenichi Okada, Osaka; Tsuyoshi Inoue, Osaka; Hiroyoshi Onishi, Osaka; Taiki Kusaka, Hyogo, all of Japan

[73] Assignees: Nitto Denko Corporation, Osaka; Kansai Paint Co., Ltd., Hyogo, both of Japan

[21] Appl. No.: 396,725

[22] Filed: Mar. 1, 1995

[30] Foreign Application Priority Data

Mar. 3, 1994 [JP] Japan ................................. 6-060173

[51] Int. Cl.$^6$ ......................................................... C09J 7/02
[52] U.S. Cl. .............................. 428/343; 428/499; 428/356
[58] Field of Search ......................... 428/343, 355, 428/499

[56] References Cited

U.S. PATENT DOCUMENTS

| | | | |
|---|---|---|---|
| 4,008,351 | 2/1977 | Inoue | 428/411 |
| 4,224,379 | 9/1980 | Ichinose | 429/461 |
| 4,906,648 | 3/1990 | Minami | 514/365 |
| 5,211,943 | 5/1993 | Azuma | 424/448 |
| 5,232,702 | 8/1993 | Pfister | 424/448 |
| 5,266,394 | 11/1993 | Diehl | 428/261 |

FOREIGN PATENT DOCUMENTS

| | | |
|---|---|---|
| 0170395 | 2/1986 | European Pat. Off. . |
| 0276666 | 8/1988 | European Pat. Off. . |
| 0327220 | 8/1989 | European Pat. Off. . |
| 0519278 | 12/1992 | European Pat. Off. . |
| 2045618 | 11/1980 | United Kingdom . |
| WO9324547 | 12/1993 | WIPO . |

*Primary Examiner*—Jenna Davis
*Attorney, Agent, or Firm*—Sughrue, Mion, Zinn, Macpeak & Seas

[57] ABSTRACT

A paint film-protective sheet comprising a supporting substrate having formed thereon a rubber-based pressure-sensitive adhesive layer containing a fatty acid glycerol ester and an antifungal agent.

5 Claims, No Drawings

PAINT-FILM PROTECTIVE SHEET

FIELD OF THE INVENTION

The present invention relates to a paint film-protective sheet which is hard to cause the deformation and mold-staining of a paint film and is suitable for the surface protection of automobile bodies and parts, coated steel plates, etc.

BACKGROUND OF THE INVENTION

In the case of loading trucks or ships with coated automobiles, the parts thereof, etc., and transporting them to remote places such as overseas, etc., an effective means for preventing the paint films from being damaged, dulled, discolored, etc., by various suspensions or collisions of dusts, rains, etc., has been desired.

Hitherto, a method of coating a coating material comprising a wax as the main component in a thickness of from 5 to 40 μm has been known as such a preventing method. However, this method has various problems that it is difficult to form the wax coating at a uniform thickness, whereby a uniform protection is not obtained; the coated film is liable to be stained and has a poor resistance to acidic rain; the wax, etc., penetrate into the coated paint film to cause a discoloration, etc.; the application of the wax coating and the removal thereof require much labors; the use of a solvent, the treatment of waste liquids, etc., are liable to cause environmental problems, etc.

On the other hand, various surface protective sheets each comprising a supporting substrate having formed thereon a pressure-sensitive adhesive layer are known, and also a surface protective sheet comprising a supporting substrate having formed thereon a radiation-curable pressure-sensitive adhesive layer having a lowered glass transition point (Tg) is proposed for use on an adherend having a paint film as disclosed in JP-A-2-199184 (the term "JP-A" as used herein means an "unexamined published Japanese patent application"). Such sheet systems can overcome the problems described above.

However, when such a surface protective sheet is adhered to the surface of the paint film of an automobile, etc., low molecular weight components contained in the paint film, such as a fatty acid glycerol ester, etc., migrate into the surface protective sheet side due to the temperature rise in an outdoor transportation, etc., whereby a step mark phenomenon occurs in the paint film to cause a problem that adhesive marks of the protective sheet clearly appear on the surface of the paint film. In particular, in a low Tg type paint film, the adhered traces having a depth of from about 0.1 to 0.5 μm usually occur during the adhesion of the protective sheet for about 10 hours under 50° C.

The present inventors have previously proposed a surface protective sheet in which a rubber-based polymer such as a polyisobutylene is used as a pressure-sensitive adhesive (EP 0 519 278 A2). This sheet is hard to cause the deformation of a paint film and does not have a problem on adhesive remaining. Thus, this sheet is a practical surface protective sheet. However, this sheet has in some cases a problem that the adhesive marks may not completely be eliminated where the paint film contains a fatty acid glycerol ester.

SUMMARY OF THE INVENTION

Accordingly, an object of the present invention is to provide a paint film-protective sheet which can prevent the occurrence of the step mark phenomenon onto a paint film by the migration of the low molecular weight components in the paint film into the paint film-protective sheet even in the case which involves the temperature rise in the outdoor transportation of automobiles, etc., whereby the adhesive marks of the protective sheet are not formed on the surface of the paint film, and is excellent in the protective property for the paint film and in the releasing property without leaving the pressure-sensitive adhesive which becomes a staining material.

According to the present invention, the above object can be realized by using a rubber-based pressure-sensitive adhesive compounded with a fatty acid glycerol ester, but in this case, since a fatty acid glycerol ester such as coconut oil, etc., is used and further since brine takes part in at a marine transportation, etc., the generation of molds due to the protective sheet is strikingly large as compared with conventional surface protective sheets.

Accordingly, another object of the present invention is also to prevent the occurrence of staining with such molds.

That is, according to the present invention, there is provided a paint film-protective film comprising a supporting substrate having formed thereon a rubber-based pressure-sensitive adhesive layer, the rubber-based pressure-sensitive adhesive layer containing a fatty acid glycerol ester and an antifungal agent.

DETAILED DESCRIPTION OF THE INVENTION

The present invention is described in detail below.

In the present invention, use of a rubber-based pressure-sensitive adhesive compounded with a fatty acid glycerol ester can prevent the migration of the low molecular weight components in the paint film into the protective sheet even in the case which involves the temperature rise in an outdoor transportation, and also the step mark phenomenon of the paint film does not occur, whereby the adhesive marks of the protective sheet are not formed on the surface of the paint film. Further, the paint film-protective sheet of the present invention is excellent in the protective property for the paint film in the state of adhering thereto the protective sheet, and also can be easily released from the paint film without leaving the pressure-sensitive adhesive which becomes a staining material.

Furthermore, in the present invention, by using an antifungal agent together with the fatty acid glycerol ester, the generation of molds can be prevented over a long period of time without losing the above-described properties, whereby staining of the paint film with molds can be prevented over a long period of time.

The paint film-protective sheet of the present invention comprises a supporting substrate having formed thereon a rubber-based pressure-sensitive adhesive layer containing a fatty acid glycerol ester and an antifungal agent.

The supporting substrate which can be used in the present invention can be any appropriate materials, and examples thereof are plastic films, porous films, papers, nonwoven fabrics, etc. The thickness of the supporting substrate is generally 300 μm or less, and preferably from 10 to 100 μm, although the invention is not limited to the thickness.

The pressure-sensitive adhesive layer can be formed by using, for example, an appropriate rubber-based pressure-sensitive adhesive comprising one or more kinds of rubber-based polymers such as a natural rubber, a polyisobutyrene, an A-B-A type block polymer, etc., as the main component and, if necessary, a tackifier or a softener. Further, the pressure-sensitive adhesive may contain appropriate additives such as a filler, a pigment, an antioxidant, a stabilizer, etc.

Examples of the more preferred rubber-based polymer from the point of the long stability of the performance are a non-curable polyisobutylene-based polymer, an A-B-A block polymer comprising a polystyrene block-ethylene/butylene copolymer block-polystyrene block, etc. In addition, the poly-isobutylene-based polymer which is preferably used is a mixture of a high molecular weight type polymer having a viscosity average molecular weight of at least 100,000 and a low molecular weight type polymer having a viscosity average molecular weight of less than 100,000 at a weight ratio of 95:5 to 50:50.

The tackifier or the softener which may be contained in the rubber-based pressure-sensitive adhesive may be any appropriate materials, but the tackifier or the softener having a good compatibility with the rubber-based polymer is preferred. Examples of the tackifier generally used are hydrocarbon resins, alkylphenol resins, terpene resins, etc.

Examples of the softener generally used are a polyisobutylene having a low molecular weight when the rubber-based polymer is a polyisobutylene, and a paraffin oil when the rubber-based polymer is the A-B-A block polymer.

Examples of the fatty acid glycerol ester compounded with the rubber-based pressure-sensitive adhesive layer in the present invention are a (mono, di, or tri)capric acid glycerol ester, a (mono, di, or tri)lauric acid glycerol ester, a (mono, di, or tri)myristic acid glycerol ester, and coconut oil. Of those, coconut oil is preferably used.

The fatty acid glycerol ester is used in the state that it is compounded with the rubber-based pressure-sensitive adhesive, and the compounding amount thereof is appropriately determined by the thickness of the pressure-sensitive adhesive layer formed. When the pressure-sensitive adhesive layer having a thickness of 15 μm is a standard, the compounding amount of the fatty acid glycerol ester is from 0.5 to 20 parts by weight, and preferably from 3 to 10 parts by weight, per 100 parts by weight of the rubber-based pressure-sensitive adhesive. If the compounding amount is over 20 parts by weight, it sometimes happens that the fatty acid glycerol ester bleeds on the surface of the pressure-sensitive adhesive layer to stain the surface of the paint film. On the other hand, if the compounding amount of the fatty acid glycerol ester is less than 0.5 part by weight, the addition effect thereof is poor and the adhesive marks are liable to form.

There is no particular restriction on the antifungal agent compounded with the rubber-based pressure-sensitive adhesive layer in the present invention, and appropriate antifungal agents can be used. By compounding an antifungal agent, staining of the paint film by the generation of molds can be prevented over a long period of time without losing the merit by compounding the fatty acid glycerol ester, such as no formation of the marks of the pressure-sensitive adhesive, the easiness of releasing, etc.

The antifungal agents can be used alone or as a mixture or 2 or more kinds thereof. The compounding amount of the antifungal agent is from 0.01 to 5 parts by weight, and preferably from 0.1 to 2 parts by weight, per 100 parts by weight of the rubber-based pressure-sensitive adhesive from the points of keeping the merit of compounding the fatty acid glycerol ester, the mold generation preventing effect, etc.

A preferred antifungal agent contains nitrogen and a halogen. Examples thereof are compounds represented by following formulae (1) to (3).

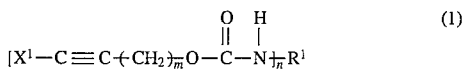

wherein $X^1$ represents a halogen atom; $R^1$ represents a hydrocarbon group; and m and n which may be the same or different each represents an integer of from 1 to 3;

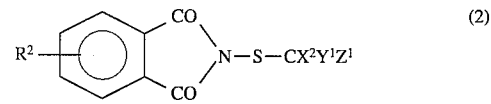

wherein $R^2$ represents hydrogen or an alkyl group having from 1 to 4 carbon atoms, and $X^2$, $Y^1$, and $Z^1$ which may be the same or different each represents hydrogen or a halogen atom, with the proviso that at least one of them is a halogen atom;

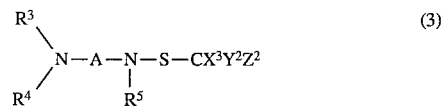

wherein $R_3$ and $R^4$ which may be the same or different each represents an alkyl group having from 1 to 4 carbon atoms; A represents a sulfonyl group, a sulfinyl group, or an acyl group; $R^5$ represents a substituted or unsubstituted phenyl group; and $X^3$, $Y^2$, and $Z^2$ which may be the same or different each represents hydrogen or a halogen atom, with the proviso that at least one of them is a halogen atom.

The antifungal agents represented by the above formulae (1) to (3) are explained in detail below.

In the carbamate compound represented by the formula (1) described above, examples of the halogen atom represented by $X^1$ are fluorine, chlorine, bromine, and iodine. Of those, bromine and iodine are preferred, and iodine is more preferred. Also, m and n each can be 1, 2 or 3. The hydrocarbon group represented by $R^1$ may be a monovalent, divalent, or trivalent group corresponding to the number of n. Further, m is preferably 1, and n is preferably 1 or 2, and more preferably 1.

Examples of the monovalent hydrocarbon group represented by $R^1$ are a straight chain or branched alkyl group having from 1 to 20 carbon atoms, such as methyl, ethyl, n-propyl, isopropyl, n-butyl, isobutyl, t-butyl, n-pentyl, n-hexyl, n-octyl, n-decyl, n-octadecyl, eicosyl, etc.; a straight chain or branched alkenyl group having from 3 to 4 carbon atoms, such as allyl, isopropenyl, 2-butenyl, 1,3-butadienyl, etc.; a cycloalkyl group having from 5 to 8 carbon atoms, such as cyclopentyl, cyclohexyl, cycloheptyl, cyclooctyl, etc.; a cycloalkenyl group having from 5 to 6 carbon atoms, such as 2-cyclopenten-1-yl, 2,4-cyclohexadien-1-yl, etc.; an aryl group such as phenyl, naphthyl, etc.; and an aralkyl group such as benzyl, 2-phenylethyl, etc.

Examples of the divalent hydrocarbon group represented by $R^1$ are an alkylene group having from 1 to 10 carbon atoms, such as methylene, ethylene, trimethylene, tetramethylene, ethylethylene, hexamethylene, decamethylene, etc.; an alkenylene group having from 3 to 9 carbon atoms, such as propenylene, 4-propyl-2-pentenylene, etc.; a cycloalkylene group such as 1,3-cyclohexylene, etc.; a cycloalkenylene such as 2,5-cyclohexadien-1,4-ylene, etc.; an arylene group such as o-phenylene, m-phenylene, p-phenylene, 1,4-naphthylene, etc.; and an alkylenediphenyl group such as 4,4'-methylenediphenyl, etc.

Examples of the trivalent hydrocarbon group represented by $R^1$ are an alkanetriyl group such as 1,2,3-propane-tri-yl, etc.

The hydrocarbon group represented by $R^1$ may be substituted with an alkyl group such as methyl, ethyl, etc.; a halogen atom such as chlorine, bromine, etc.; or an alkoxy group such as methoxy, ethoxy, etc. Preferred hydrocarbon groups represented by $R^1$ have from 1 to 20 carbon atoms.

The preferred carbamate compound represented by the formula (1) is that the hydrocarbon group represented by $R^1$ is a monovalent or divalent hydrocarbon group.

Specific examples of the carbamate compound wherein $R^1$ is a monovalent hydrocarbon group are carbamate compounds wherein the hydrocarbon group represented by $R^1$ is an alkyl group such as 3-iodo-2-propynyl methylcarbamate, 3-iodo-2-propynyl ethylcarbamate, 3-iodo-2-propynyl propylcarbamate, 3-iodo-2-propynyl butylcarbamate, 3-iodo-2-propynyl t-butylcarbamate, 3-iodo-2-propynyl hexylcarbamate, 3-iodo-2-propynyl octylcarbamate, 4-iodo-3-butynyl butylcarbamate, etc.

Specific examples of the preferred carbamate compound wherein the hydrocarbon group represented by $R^1$ is monovalent are a carbamate compound wherein the hydrocarbon group represented by $R^1$ is an alkenyl group, such as 3-iodo-2-propynyl allylcarbamate; a carbamate compound wherein the hydrocarbon group represented by $R^1$ is a cycloalkyl group, such as 3-iodo-2-propynyl cyclohexylcarbamate; a carbamate compound wherein the hydrocarbon group represented by $R^1$ is an aryl group, such as 3-iodo-2-propynyl phenyl carbamate, 3-iodo-2-propynyl 4-chlorophenylcarbamate or 3-iodo-2-propynyl 3-methylphenylcarbamate; a carbamate compound wherein the hydrocarbon group represented by $R^1$ is an aralkyl group, such as 3-iodo-2-propynyl benzyl carbamate; and the like.

On the other hand, specific examples of the preferred carbamate compound wherein the hydrocarbon group represented by $R^1$ is divalent are a carbamate compound wherein the hydrocarbon group represented by $R^1$ is an alkylene group, such as di(3-iodo-2-propyl) hexamethylenecarbamate; a carbamate compound wherein the hydrocarbon group represented by $R^1$ is an alkylenediphenyl group, such as di(3-iodo-2-propynyl) 4,4'-methylenediphenylcarbamate; and the like.

The more preferred carbamate compounds are the carbamate compounds wherein the hydrocarbon group represented by $R^1$ is an alkyl group having from 1 to 5 carbon atoms, such as ethyl or butyl, and of those, a carbamate compound wherein the hydrocarbon group represented by $R^1$ is butyl, such as 3-iodo-2-propynyl butylcarbamate is most preferred.

In the compound represented by the formula (2) described above, $R^2$ represents hydrogen atom or an alkyl group having from 1 to 4 carbon atoms. Examples of the alkyl group are methyl, ethyl, n-propyl, isopropyl, n-butyl, and isobutyl. Further examples of the halogen atom represented by $X^2$, $Y^1$, and $Z^1$ are fluorine, chlorine, bromine, and iodine, and at least one of $X^2$, $Y^1$, and $Z^1$ is fluorine, chlorine, bromine, or iodine. Thus, two or all of $X^2$, $Y^1$, and $Z^1$ may be halogen atoms In addition, $X^2$, $Y^1$, and $Z^1$ may be the same or different.

Examples of the preferred compound represented by the formula (2) are N-(fluorodichloromethylthio)phthalimide, N-(dichloromethylthio) phthalimide, N-(dibromomethylthio)-phthalimide, and N-(diiodomethylthio) phthalimide. Of those compounds, N-(fluorodichloromethylthio) phthalimide is preferred.

In the compound represented by the formula (3) described above, examples of the alkyl group having from 1 to 4 carbon atoms represented by $R^3$ and $R^4$ are methyl, ethyl, n-propyl, isopropyl, n-butyl, isobutyl, etc. $R^3$ and $R^4$ may be the same or different. Also, A represents a sulfonyl group, a sulfinyl group, or an acyl group, and of those, a sulfonyl group is preferred.

In the substituted or unsubstituted phenyl group represented by $R^5$ in the formula (3), examples of the substituted phenyl group are a mono-substituted group, a di-substituted group, etc.

In the-case of the mono-substituted phenyl group, the substituted position may be any desired position, and in the di-substituted phenyl group, the substituted positions may be any of an ortho-position, a meta-position or a para-position. Examples of the substituent are an alkyl group having from 1 to 4 carbon atoms, such as methyl, ethyl, n-propyl, isopropyl, n-butyl or isobutyl; and the like. The preferred substituted phenyl group is 4-methylbenzene. In addition, $X^3$, $Y^2$, and $Z^2$ in the formula (3) are the same as in $X^2$, $Y^1$, and $Z^1$ in the formula (2), respectively.

Examples of the preferred compound represented by the formula (3) are N,N-dimethyl-N'-phenyl-N'-(fluorodichloromethylthio)-sulfamide and N,N-dimethyl-N'-(4-methylphenyl)-N'-(fluorodichloromethylthio)-sulfamide.

The paint film-protective sheet of the present invention can be formed according to a conventional adhesive sheet-forming method such as a method of coating a supporting substrate with a solvent solution or a hot-melt liquid of the rubber-based pressure-sensitive adhesive compounded with the fatty acid glycerol ester and the antifungal agent, a method of transferring the pressure-sensitive adhesive layer formed on a separator onto a supporting substrate, etc.

The thickness of the pressure-sensitive adhesive layer formed may be appropriately determined, but is generally 200 μm or less, and preferably from 5 to 50 μm. The pressure-sensitive adhesive layer is, if necessary, protected by pre-fixing thereto a separator, etc., before use.

The paint film-protective sheet of the present invention is preferably used to protect the surface of adherends having a paint film, such as automobile bodies and the parts thereof, metal plates such as steel plates, etc., or shaped articles thereof, coated with a paint film such as a melamine-alkyd type, melamine-acryl type, or urethane type paint film, from impinging of fine matters, chemicals, etc. In particular, the paint film-protective sheet can be advantageously used in the case that the sheet is placed under circumstances which are liable to generate molds, such as the case which involves a temperature rise in an outdoor transportation, etc., the case that the protective sheet is adhered over a long period of time, etc.

The present invention is described below in more detail by reference to the following examples and comparative examples, but it should be understood that the invention is not construed as being limited thereto. Unless otherwise indicated, all percents, parts, ratios and the like are by weight.

EXAMPLE 1

A toluene solution of a rubber-based pressure-sensitive adhesive composed of a mixture of 75 parts of a polyisobutylene having a viscosity average molecular weight of 1,000,000 and 25 parts of a polyisobutylene having a viscosity average molecular weight of 80,000 was compounded with 5 parts of coconut oil and 0.1 part of an antifungal agent shown below, the resulting liquid was coated on a film having a thickness of 40 μm composed of polypropylene/polyethylene (9/1 by weight ratio), and dried at 80° C. for 2 minutes to obtain a paint film-protective sheet having a pressure-sensitive adhesive layer having a thickness of 15 μm.

The antifungal agent used was a compound represented by the formula $IC\equiv CCH_2OC(O)NH(CH_2)_3CH_3$ (Coatcide 123, trade name, made by Takeda Chemical Industries, Ltd.) was used.

EXAMPLE 2

A paint film-protective sheet was obtained in the same manner as in Example 1 except that a compound represented by the following formula (Coatcide CS, trade name, made by Takeda Chemical Industries, Ltd.) was used as the antifungal agent.

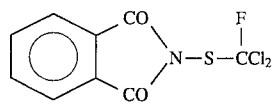

EXAMPLE 3

A paint film-protective sheet was obtained in the same manner as in Example 1 except that a compound represented by the following formula (Coatcide TW, trade name, made by Takeda Chemical Industries, Ltd.) was used as the antifungal agent.

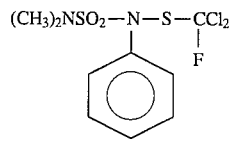

EXAMPLE 4

A paint film-protective sheet was obtained in the same manner as in Example 1 except that trilauric acid glycerol ester was used in place of coconut oil.

EXAMPLE 5

A paint film-protective sheet was obtained in the same manner as in Example 1 except that a mixture of 100 parts of an A-B-A block polymer (Kraton G-1657, trade name, made by Shell Chemical Co.) composed of a polystyrene block, an ethylene-butylene copolymer block, and a polystyrene block and 40 parts of a hydrogenated petroleum resin (Arcon P-100, trade name, made by Arakawa Kagaku K. K.) was used as the rubber-based pressure-sensitive adhesive.

COMPARATIVE EXAMPLE 1

A paint film-protective sheet was obtained in the same manner as in Example 1 except that the antifungal agent was not used.

COMPARATIVE EXAMPLE 2

A paint film-protective sheet was obtained in the same manner as in Example 5 except that the antifungal agent was not used.

Evaluation Tests

Each of the paint film-protective sheets obtained in the examples and the comparative examples was subjected to the following tests.

Adhesive Remaining:

The paint film-protective sheet was adhered to a plate having an alkyd-melamine paint film having a glass transition point of 60° C. containing a fatty acid glycerol ester. The resulting plate was placed in an atmosphere of 80° C. for 24 hours, taken out therefrom, and then allowed to stand for 3 hours at room temperature. The paint film-protective sheet was stripped off, and the presence of the pressure-sensitive adhesive on the plate, in particular, the presence of the pressure-sensitive adhesive remained on the portion of the paint film corresponding to the peripheral portion of the paint film-protective sheet, was examined.

Adhesive Mark:

The alkyd-melamine paint film after the above adhesive remaining test was observed, and the presence of the adhesive mark in the paint film, in particular, the presence of the adhesive mark of the portion of the paint film corresponding to the peripheral portion of the paint film-protective sheet, was visually examined. In this test, when the adhesive mark (concaved potion) of the paint film caused by the migration of the fatty acid glycerol ester contained in the alkyd-melamine paint film into the paint film-protective sheet was not observed, the case was evaluated as "none" and when the adhesive mark was observed, the case was evaluated as "found".

Mold Generation:

The paint film-protective sheet was adhered to a Saburo agar culture medium. A mold liquid containing culture medium components was sprayed thereon, and cultivated at 28° C. for 4 weeks. The growth of molds on the sample was visually observed. In this test, when the growth of molds on the surface of the sample was not observed, the case was evaluated as "none", and when the growth of molds was observed even slight, the case was evaluated as "found".

The results obtained are shown in the table below.

TABLE

|  | Example |  |  |  |  | Comparative Example |  |
|---|---|---|---|---|---|---|---|
|  | 1 | 2 | 3 | 4 | 5 | 1 | 2 |
| Adhesive remaining | None | None | None | None | None | None | None |
| Adhesive Mark | None | None | None | None | None | None | None |
| Mold growth | None | None | None | None | None | Found | Found |

According to the paint film-protective sheet of the present invention, the migration of the low molecular weight components in the paint film into the paint film-protective sheet can be prevented even in the cases that the glass transition point of the paint film is low and the temperature of the paint film rises; the occurrence of the step mark phenomenon onto the paint film can be prevented, whereby the adhesive marks of the protective sheet are not formed on the surface of the paint film; and the generation of molds can be prevented over a long period of time, whereby mold-staining does not form on the paint film. Further, the paint film-protective sheet of the present invention is excellent in the paint film-protective property in the adhered state and can be easily released from the paint film without forming the adhesive remaining which becomes a staining material and without causing mold staining.

While the invention has been described in detail and with reference to specific embodiments thereof, it will be apparent to one skilled in the art that various changes and modifications can be made therein without departing from the spirit and scope thereof.

What is claimed is:

1. A sheet for protecting a painted surface having a low glass transition point, said sheet comprising a substrate having formed thereon a rubber-based pressure-sensitive adhesive layer containing a fatty acid glycerol ester and an antifungal agent.

2. A sheet as claimed in claim 1, wherein the fatty acid glycerol ester is contained in an amount of from 0.5 to 20 parts by weight per 100 parts by weight of the rubber-based pressure-sensitive adhesive, and the antifungal agent is contained in an amount of from 0.01 to 5 parts by weight per 100 parts by weight of the rubber-based pressure-sensitive adhesive.

3. A sheet as claimed in claim 1, wherein the fatty acid glycerol ester is coconut oil.

4. A sheet as claimed in claim 1, wherein the antifungal agent is at least one compound selected from the group consisting of compounds represented by the following formulae (1) to (3):

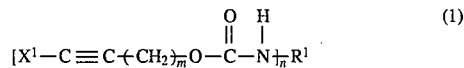
(1)

wherein $X^1$ represents a halogen atom, $R^1$ represents a hydrocarbon group, and m and n which may be the same or different each represents an integer of from 1 to 3;

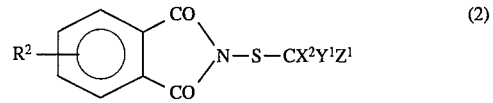
(2)

wherein $R^2$ represents hydrogen or an alkyl group having from 1 to 4 carbon atoms, and $X^2$, $Y^1$, and $Z^1$ which may be the same or different each represents hydrogen or a halogen atom, with the proviso that at least one of them is a halogen atom;

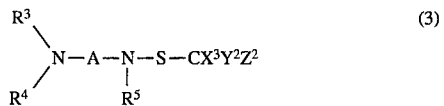
(3)

wherein $R^3$ and $R^4$ which may be the same or different each represents an alkyl group having from 1 to 4 carbon atoms, A represents a sulfonyl group, a sulfinyl group, or an acyl group, $R^5$ represents a substituted or unsubstituted phenyl group, and $X^3$, $Y^1$, nd $Z^2$ which may be the same or different each represents hydrogen or a halogen atom, with the proviso that at least one of them is a halogen atom.

5. A sheet as claimed in claim 1, wherein the rubber-based pressure-sensitive adhesive comprises a non-curable polyisobutylene polymer or an A-B-A block copolymer comprising a polystyrene block, an ethylene-butylene copolymer block, and a polystyrene block as the main component.

* * * * *